(12) United States Patent
Fornara et al.

(10) Patent No.: US 6,617,301 B1
(45) Date of Patent: Sep. 9, 2003

(54) MIXTURES OF SURFACTANTS USED AS WETTING AGENTS AND/OR EMULSIFIERS IN AGROCHEMICAL PREPARATIONS

(75) Inventors: Dario Fornara, Novara (IT); Peter Bohus, Caronno Varesino (IT); Alberto Colombo, Lissone (IT)

(73) Assignee: Lamberti S.p.A., Albizzate (IT)

( * ) Notice: Subject to any disclaimer, the term of this patent is extended or adjusted under 35 U.S.C. 154(b) by 0 days.

(21) Appl. No.: 09/979,760

(22) PCT Filed: May 16, 2000

(86) PCT No.: PCT/EP00/04375

§ 371 (c)(1),
(2), (4) Date: Nov. 24, 2001

(87) PCT Pub. No.: WO00/69261

PCT Pub. Date: Nov. 23, 2000

(30) Foreign Application Priority Data

May 18, 1999 (IT) .......................................... MI99A1086

(51) Int. Cl.$^7$ ........................... A01N 25/30; C11D 1/83; C11D 3/22
(52) U.S. Cl. ...................... 510/470; 510/199; 510/437; 510/488; 510/491; 424/405; 427/4
(58) Field of Search ................................ 510/199, 437, 510/470, 488, 491; 424/405; 427/4

(56) References Cited

U.S. PATENT DOCUMENTS

| | | | | |
|---|---|---|---|---|
| 3,219,656 A | * | 11/1965 | Boettner ..................... | 260/210 |
| 3,547,828 A | * | 12/1970 | Mansfield et al. .......... | 252/351 |
| 3,839,318 A | * | 10/1974 | Mansfield ................ | 260/210 R |
| 4,797,481 A | * | 1/1989 | Garlisi et al. ................ | 536/116 |
| 4,888,325 A | * | 12/1989 | Schroeder et al. ............. | 514/25 |
| 5,273,953 A | * | 12/1993 | Szekely et al. ............. | 504/116 |
| 5,385,750 A | * | 1/1995 | Aleksejczyk et al. .......... | 427/4 |
| 5,783,692 A | * | 7/1998 | Kirby et al. ............. | 536/123.1 |
| 5,811,386 A | * | 9/1998 | Mueller et al. .............. | 510/535 |
| 2003/0006040 A1 | * | 1/2003 | McGregor et al. .......... | 166/312 |

FOREIGN PATENT DOCUMENTS

| | | | | |
|---|---|---|---|---|
| EP | 258814 | * | 3/1988 | ........... C07H/15/04 |
| EP | 510564 | * | 10/1992 | ........... C07H/15/04 |
| WO | WO 00/69261 | * | 11/2000 | ........... A01N/25/30 |

OTHER PUBLICATIONS

"Citric Ester Surfactants". P.J. Borchert et al. Proceeding of the World Surfactants Congress–Munich 1984, vol. 2, pp. 147–154. No month given.*

* cited by examiner

Primary Examiner—Yogendra N. Gupta
Assistant Examiner—Brian P. Mruk
(74) Attorney, Agent, or Firm—Abelman, Frayne & Schwab

(57) ABSTRACT

The present invention relates to surfactant mixtures with improved wetting and/or emulsifying properties for use in agrochemical preparations, comprising: A) at least an alkylpolyglucoside, B) at least an anionic derivative of an alkylpolyglucoside, and C) at least an anionic derivative of a fatty alcohol.

25 Claims, No Drawings

MIXTURES OF SURFACTANTS USED AS WETTING AGENTS AND/OR EMULSIFIERS IN AGROCHEMICAL PREPARATIONS

FIELD OF THE INVENTION

The present invention relates to surfactant mixtures used as wetting agents and/or as emulsifiers in agrochemical preparations, particularly in pesticide compositions.

STATE OF THE ART

The pesticide active ingredients—according to the characteristics of the actives and of their intended applications—can be formulated as dusts, wettable powders, dispersible granules, suspension concentrates, emulsifiable concentrates, emulsions and concentrated solutions, and their application as formulated products on soil, seeds or plant foliage is generally carried out with aqueous spray in form of solution, suspension or emulsion.

Surfactants are commonly used in order to disperse and suspend the solid substances, or to emulsify the oily liquids in water, forming suspensions or stable emulsions. The surfactants help the formation of aqueous dispersions of compounds insoluble in water. Moreover the surfactants reduce the surface tension between aqueous spray and the material (soil, seeds, foliage) to be treated, thus favouring the spreading of droplets on the treated surface and the penetration of the active ingredient into the materials.

Among surfactants, which can be used for the aforementioned purposes, the aliphatic polyglucosides have been known for a long time. These materials offer several advantages due to their low toxicity and good biodegradability, and even have certain fungicide, insecticide, and acaricide activities. Due to these features, the organic polyglucosides provide, in agrochemical formulations and applications, a wider spectrum of functions, since other equivalent traditional surfactants are normally used only as wetting agents and/or emulsifiers.

For instance, U.S. Pat. No. 4,888,325 describes pesticide compositions that contain alkylglucosides, alone or in combination with other surfactants. However, such compositions show weak wetting performance and cannot sufficiently reduce the interfacial tension between the aqueous spray and the material on which said spray is applied.

U.S. Pat. No. 5,385,750 describes the use of aliphatic polyglucosides as co-adjuvant in pesticide formulations in combination with fatty alcohol. According to U.S. Pat. No. 5,385,750 the addition of fatty alcohol to the alkylpolyglucosides increases its wetting performance, favouring the penetration of the pesticide active ingredient into biological materials, even when the treated surface layers are waxy or oily as in the case of foliage.

On the other hand, the presence of a fatty alcohol creates considerable drawbacks: it gives bad odours and causes a noticeable lowering of the emulsifying ability of the alkylpolyglucosides.

Therefore, it is still an unresolved problem to obtain compositions based on aliphatic polyglucosides having better wetting properties, maintaining good emulsifying characteristics, without the drawbacks experienced with the known products as described above.

SUMMARY OF THE INVENTION

Now the Applicant has found that the use, as wetting agent and/or emulsifier, of a mixture comprising at least an alkylpolyglucoside, at least an anionic derivative of an alkylpolyglucoside and at least an anionic derivative of a fatty alcohol, in suitable weight ratio, has unexpected advantages in the application of agrochemical preparations on soil, seeds and plants, particularly when aqueous sprays of pesticide formulations are used.

These surfactant mixtures show the required efficacy in the formation of stable systems with water and organic substances and, moreover, they increase the penetration of the pesticide active ingredient into biological materials, due to a superior wetting power as compared to that of aliphatic polyglucosides used alone.

Additionally, the substances contained in the present mixtures are quickly biodegradable and satisfy the request of low toxicity for the mammals and low irritating effect in contact with the epidermis, thus being suitable for the use in pesticide preparations to be applied on edible plants; the mixtures of the present invention are indeed free of harmful or toxic by-products, like amines, ethylene oxide, 1,4-dioxane, alkyl phenols, etc.

Therefore the subject of the present invention is a surfactant mixture suitable for the use as wetting agent and/or emulsifier in pesticide agrochemical compositions, characterised by comprising:

A) at least an alkylpolyglucoside,

B) at least an anionic derivative of an alkylpolyglucoside, and

C) at least an anionic derivative of a fatty alcohol.

Further subjects of the present invention are the aqueous compositions of pesticides comprising such surfactant mixture, and their use in agriculture for the treatment of seeds, plants and soil.

The characteristics and the advantages of the surfactant mixtures according to the present invention will be illustrated in detail in the following description.

DETAILED DESCRIPTION OF THE INVENTION

The present surfactant mixture comprises at least an alkylpolyglucoside, at least an anionic derivative of an alkylpolyglucoside and at least an anionic derivative of a fatty alcohol.

Examples of alkylpolyglucosides, according to the aim of the present invention are the aliphatic alkylpolyglucosides represented by the following formula (I)

$$R\text{—}O\text{—}(G)_x \qquad (I)$$

where:

R is a saturated or unsaturated aliphatic group having from 6 to 20 carbon atoms, linear or branched;

O is an oxygen atom;

G is a residue of a reducing saccharide connected to R—O by means of an ethereal O-glycosidical bond;

x is a number from 1 to 10, representing the average degree of oligomerization of G.

Preferably R is an alkyl group having from 8 to 16 atoms of carbon, G is a residue of a reducing saccharide and x is a number between 1 and 2.

The preferred alkylpolyglucosides, according to the invention, are compounds of formula (I) in which G is a residue of glucose.

The compounds of formula (I) are known, as well as their methods of preparation, and are for instance described in U.S. Pat. Nos. 3,219,656, 3,547,828 and 3,839,318.

Preferred compounds of formula (I) reported above are commercially available products and are endowed with an high biodegradability.

Examples of anionic derivatives of alkylpolyglucosides according to the aim of the present invention are compounds represented by the following formula (II)

$$[R'—O—(G)_x]_n—(D)_y \qquad (II)$$

where:

R' is a aliphatic group, saturated or unsaturated, linear or branched, having from 6 to 20 atoms of carbon, preferably from 8 to 16 atoms of carbon;

G is a residue of a reducing saccharide, preferably of glucose, connected to R'—O by means of an ethereal O-glycosidical bond;

O is an oxygen atom;

D is an acyl residue connected to an oxygen atom of the residue G, and derived from a bicarboxylic acid or a polycarboxylic acid having an aliphatic chain from 2 to 8 carbon atoms, linear or branched, saturated or unsaturated, not substituted or substituted with one or more hydroxyl groups, and in which at least one carboxylic group is salified or in acid form;

n is a number between 1 and m−1, where m is the number of carboxylic groups in the acid that originates D;

x has the same meaning as described above for the compounds of formula (I);

y is a number from 1 to 10 representing the degree of average esterification of $(G)_x$.

Preferred anionic derivatives of alkylpolyglucosides according to the present invention, are compounds of formula (II), in which R' is an alkyl group having from 8 to 16 atoms of carbon and D is the acyl residue of a carboxylic acid selected from the group consisting of citric acid, tartaric acid, maleic acid and malic acid.

The above mentioned anionic derivatives of alkylpolyglucosides of formula (II) are known and they can be prepared as described, for example, in EP 258 814, or in EP 510 564.

Examples of anionic derivatives of fatty alcohols according to the present invention are represented by the following formula (III)

$$R''—O—D' \qquad (III)$$

and they can be prepared by esterification of a carboxylic acid with a fatty alcohol of formula R''—OH, where:

R'' is an aliphatic group, saturated or unsaturated, linear or branched, having from 6 to 20 atoms of carbon, preferably from 8 to 16 atoms of carbon;

O is an oxygen atom;

D' is an acyl residue of a bicarboxylic acid or of a polycarboxylic acid having an aliphatic chain with from 2 to 8 atoms of carbon, saturated or unsaturated, linear or branched, not substituted or substituted with one or more hydroxyl groups, and in which at least one carboxyl group is salified or in its acid form.

Preferred anionic derivatives of fatty alcohols according to the present invention are compounds of formula (III) in which D' is an acyl residue of a carboxylic acid selected from the group consisting of citric acid, tartaric acid, malic acid and maleic acid.

An example of preparation of the anionic derivatives of fatty alcohols of formula (III) has been reported in the article "Citric Ester Surfactants"—P. J. Borchert et al.—Proceeding of the World Surfactants Congress—Munich 1984, vol. 2, pag. 147. Particularly relevant for the realisation of the present invention are the anionic derivatives of alkylpolyglucosides (II) and the anionic derivatives of fatty alcohol (III) in which D and D' are acyl residues of citric acid with at least one carboxylic group salified, preferably in the form of sodium salt.

In the surfactant mixture according to the present invention, the R group in the compound of formula (I), the R' group in the compound of formula (II) and the R'' group of the fatty alcohol of formula (III) can be equal or different from one another; surfactant mixtures in which R=R'=R'' have wetting and emulsifying power particularly high.

Similarly, in the surfactant mixture according to the present invention, the D group in the compound of formula (II) and the D' group in the compound of formula (III) can be equal or different from one another; the surfactant mixtures in which D=D' have wetting and emulsifying power particularly high.

According to the present invention, particularly preferred are surfactant mixtures in which R=R'=R'' and simultaneously D=D'.

In the present surfactant mixture composition the quantity of each component ranges between 1 and 98% by weight with respect to the total weight of the mixture.

According to a preferred embodiment of the present invention, the surfactant mixture composition, expressed as percentage by weight of each component with respect to the total weight of the mixture, is the following:

| | |
|---|---|
| A) alkylpolyglucoside of formula (I) | 20–60% |
| B) anionic derivative of alkylpolyglucoside of formula (II) | 20–50% |
| C) anionic derivative of fatty alcohol of formula (III) | 10–30% |

The present surfactant mixture may comprise from 0 to 97% by weight of water with respect to the total weight of the mixture.

The surfactant mixture of the present invention can be used to formulate active ingredients in form of wettable powders, dispersible granules, concentrated suspensions, concentrated emulsions, microemulsions, macroemulsions, microencapsulated products, solutions, etc., thus obtaining a composition to be applied as such, or in a diluted form with water or with other appropriate solvent at the required dilution ratio; said composition can be prepared at the required dilution right before use too.

In a particular embodiment of the invention, it is generally preferred to add the present surfactant mixture to the formulated pesticide, and then to dilute with water to the desired concentration in order to obtain an aqueous sprayable composition of the formulated pesticide.

According to a particular embodiment of the present invention, the agrochemical compositions comprising the surfactant mixture, comprise at least an active ingredient, for example with pesticide action, and a carrier, for instance water; preferably, in such compositions the quantity of surfactant mixture is from 1 to 90% in weight, with respect to the total weight of the composition, the quantity of the active ingredient is from 1 and 90% by weight, while the quantity of carrier makes up the balance of the composition.

Said agrochemical compositions can further comprise:

one or more active ingredients with various functions, for instance insecticide, acaricide, fungicide, nematocide, disinfectant, herbicide, fertilizer or micronutrient;

other surfactants, besides those of the surfactant mixture subject of the invention;

other products, such as antifoam agents, antifreeze agents, dyes, stabilisers and buffers;

usual additives of agrochemical compositions.

Preferably, the present surfactant mixture is used in aqueous spray formulations of pesticides, comprising for example:

said surfactant mixture in an amount from 0.1 to 20% by weight with respect to the total weight of the composition, preferably from 1 to 10% by weight;

the concentrated formulation of the pesticide active ingredient, in quantity between 0.1 and 20% by weight;

water, and, optionally, other concentrated formulations of active ingredients, micronutrients, other surfactants and/or other additives commonly used in the agrochemical compositions, in such an amount which makes up the balance of the composition.

Said agrochemical compositions can comprise pesticide active compounds, such as Acephate, Acetochlor, Alachlor, Alphacypermethrin, Amitraz, Atrazine, Benomyl, Bentazon, Bromacil, Captan, Carbaryl, Carbendazim, Carbofuran, Carboxin, Chloridazon, Chlorpyriphos, Chlorthalonil, Chlortoluron, Copper oxychloride, Copper oxyquinolate, Cypermethrin, Cyromazine, Dalapon, Deltamethrin, Diazinone, Dicamba, Dichlorprop, Dicofol, Dimethoate, Dinocap, Diuron, Dodine, Endosulfan, Ethofumesate, Ethylparathion, Fenitrothion, Fenthion, Fentin Hydroxide, Fluometuron, Folpet, Fosetyl-Al, Glufosinate, Glyphosate, Lindane, Linuron, Malathion, Mancozeb, MCPA, MCPB, Metalaxyl, Methamidophos, Methomyl, Methylparathion, Metobromuron, Metolachlor, Naled, Oxadiazon, Paraquat, Pendimethalin, Permethrin, Phenmedipham, Pyperonilbutoxide, Pirethrum, Propachlor, Propanil, Propiconazol, Propisochlor, Propoxur, Quizalofop-P-tefuryl, Sethoxydim, Simazine, Sulphur, Temephos, Tetraconazol, Tetramethrin, Thiophanate methyl, Thiram, Triadimefon, Triadimenol, Trifluralin, Vinclozolin, Zineb, Ziram, and their mixtures.

The surfactant mixture of the present invention is particularly suited for agrochemical formulations comprising N-(phosphonomethyl)glycine (Glyphosate) or its salts, preferably the isopropylammonium salt of N-(phosphonomethyl)glycine (Glyphosate isopropylammonium), which is from here on referred to as Glyphosate IPA.

The Applicant has found that the use of said surfactant mixture in dilutable with water or aqueous compositions of pesticides has an emulsifying effect and wetting performance, which can help the formation of an homogeneous dispersion of the pesticide in water, thus accelerating its penetration in the treated biological materials (soil, seeds or plant foliage), in an unexpectedly higher degree as compared to the known prior art where only alkylpolyglucosides are used.

The aforementioned characteristics of said surfactant mixtures are determined by measurement of the superficial tension and determinations of the wetting power, as illustrated in the following Examples.

The following examples will serve to further illustrate the invention and are intended to be illustrative and not limiting of the present invention. The following experimental examples were carried out with the surfactant mixtures of the present invention and using the following prior art products:

an aqueous solution (70% water) of an alkylpolyglucoside with a degree of glucose oligomerization of 1.2, free alcohol content of less than 1%, and with the following composition of the lipophilic chain:

C10=26.0%
C12=50.0%
C14=23.5%
C16=0.5%.

This aqueous solution is referred to from here on as ALKPG/30.

ethoxylated tallow amine, with an average ethoxylation degree of 15 EO mole/mole (EMULSON® GPE 3 SS, CESALPINIA SpA).

EXAMPLE 1

Preparation of the Surfactant Mixture of the Invention (Mixture 1)

a) Preparation of the Alkylpolyglucoside

In a reaction vessel equipped with heating, cooling, strirrer, thermometer, a system of introduction of the reagents, such reaction vessel being connected both to a cooler provided of collector of water of reaction, and to a vacuum pump, the following components are added, under stirring: 930 g (5 mol) of a mixture of decyl alcohol, dodecyl alcohol, tetradecyl alcohol and hexadecyl alcohol with ratio 26:50:23.5:0.5, and 1.4 g of p-toluenesulphonic acid monohydrate. The temperature is set at 120° C. while the vacuum pump applies a pressure of 50–60 mm Hg. At temperature of 120° C., 180 g (1 mol) of anhydrous glucose are added, in constant portions every 10 minutes, in a period of about 120 minutes. At the end of the last addition the temperature of 120° C. is maintained for further 30 minutes, then the temperature is decreased to 50–60° C. and the neutralisation is carried out with 1 g of a 30% solution of sodium hydroxide. The obtained product is an alkyl (C10–C12–C14–C16)polyglucoside containing about 75% of free fatty alcohol. By means of distillation on thin layer at 150° C. and at a pressure of 2 mmHg, the main part of unreacted fatty alcohol is distilled off, thus yielding an alkyl(C10–C12–C14–C16)polyglucoside containing about 27% of free fatty alcohol. The degree of glucose oligomerization is about 1.2.

b) Preparation of the Ester and Its Salification

In a reactor analogous to that used in phase a), 100 g of the product prepared in the phase a) are introduced. The temperature is adjusted to 130° C. under stirring; at this temperature 63.7 g of citric acid are added over a period of about 1 hour. The reaction mixture is maintained at 130° C. until the acidity number reaches 236 (±5) mg/g of KOH. Then the reaction mixture is cooled down to 110–115° C. and a dilution is made with 327.6 g of water. The temperature is furthermore decreased to 30° C. and 88.7 g of a 30% aqueous solution of caustic soda, are added, over a period of about 1 hour. In this way, about 570 g of an 30% aqueous solution is obtained, where the dry fraction consists of about 66% of alkylpolyglucoside citric ester sodium salt and of about 33% of fatty alcohol citric ester sodium salt.

c) Final Mixing

To 120 g of the mixture of esters obtained in the b phase) the following quantities of alkylpolyglucoside ALKPG/30 are added under stirring in order to obtain homogeneous products:

80 g of ALKPG/30 (Mixture 1.1)
146.7 g of ALKPG/30 (Mixture 1.2)
280 g of ALKPG/30 (Mixture 1.3)
680 g of ALKPG/30 (Mixture 1.4)

EXAMPLE 2
Preparation of the Surfactants Mixture of the Invention (Mixture 2)

a) Preparation of the Alkylpolyglucoside.

In a reaction vessel equipped with heating, cooling, stirrer, thermometer, a system of introduction of the reagents, such reaction vessel being connected both to a cooler provided of collector of water of reaction, and to a vacuum pump, the following components are added, under stirring: 930 g (5 mol) of a mixture of decyl alcohol, dodecyl alcohol, tetradecyl alcohol and hexadecyl alcohol with ratio 26:50:23.5:0.5, and 1.4 g of p-toluenesulphonic acid monohydrate. The temperature is set at 120° C. while the vacuum pump applies a pressure of 50–60 mm Hg. At temperature of 120° C., 180 g (1 mol) of anhydrous glucose are added in portions in about 120 minutes. At the end of the last addition the temperature of 120° C. is maintained for another 30 minutes, then the temperature is decreased to 50–60° C. and the neutralisation is carried out with 1 g of a 30% solution of sodium hydroxide. The obtained product is an alkyl (C10–C12–C14–C16)polyglucoside containing about 75% of free fatty alcohol. By means of distillation on thin layer at 150° C. and at a pressure of 2 mmHg, the main part of unreacted fatty alcohol is distilled off, thus yielding an alkyl(C10–C12–C14–C16)polyglucoside containing about 28% of free fatty alcohol. The degree of glucose oligomerization is about 1.2.

b) Preparation of the Ester and Its Salification

In a reactor analogous to that used in phase a), 100 g of the product prepared in the phase a) are introduced. The temperature is adjusted to 130° C. under stirring; at this temperature 50.2 g of tartaric acid are added over a period of about 1 hour. The reaction mixture is maintained at 130° C. until the acidity number reaches 130±3 mg/g of KOH. Then the reaction mixture is cooled down to 110–115° C. and a dilution is made with 316.4 g of water. The temperature is furthermore decreased to 30° C. and 44.7 g of a 30% aqueous solution of caustic soda, are added, over a period of about 1 hour. In this way, about 570 g of an 30% aqueous solution is obtained, where the dry fraction consists of about 66% of alkylpolyglucoside tartaric acid ester sodium salt and about 33% of fatty alcohol tartaric acid ester sodium salt.

c) Final Mixing

To 80 g of the mixture of esters obtained in the b phase) the following quantities of alkylpolyglucoside ALKPG/30 are added under stirring in order to obtain homogeneous products:

120 g of ALKPG/30 (Mixture 2.1)
186.7 g of ALKPG/30 (Mixture 2.2)
320 g of ALKPG/30 (Mixture 2.3)
720 g of ALKPG/30 (Mixture 2.4)

EXAMPLE 3
Preparation of Pesticide Compositions Based on Glyphosate IPA

The surfactant mixtures prepared as described in the Examples 1 and 2, and the products ALKPG/30 and EMULSON GPE 3 SS have been used for the preparation of pesticide compositions comprising Glyphosate IPA.

These compositions have been prepared by adding the aqueous surfactant mixture and the solution of the active ingredient in the desired quantities into water reported in Table 1. As active ingredient a commercially available aqueous solution is used, containing 46.2 % Glyphosate IPA. In all these compositions the total amount of surfactants is 1% by weight.

The prepared compositions are given in the following Table 1.

TABLE 1

| Composition | Components | Quantity (% by wt.) |
| --- | --- | --- |
| 1 (Comparison) | Glyphosate IPA | 1 |
|  | Water | 99 |
| 2 (Comparison) | Glyphosate IPA | 1 |
|  | ALKPG/30 | 1 |
|  | Water | 98 |
| 3 | Glyphosate IPA | 1 |
|  | Mixture 1.4 | 1 |
|  | Water | 98 |
| 4 | Glyphosate IPA | 1 |
|  | Mixture 1.3 | 1 |
|  | Water | 98 |
| 5 | Glyphosate IPA | 1 |
|  | Mixture 1.2 | 1 |
|  | Water | 98 |
| 6 | Glyphosate IPA | 1 |
|  | Mixture 1.1 | 1 |
|  | Water | 98 |
| 7 | Glyphosate IPA | 1 |
|  | Mixture 2.4 | 1 |
|  | Water | 98 |
| 8 | Glyphosate IPA | 1 |
|  | Mixture 2.3 | 1 |
|  | Water | 98 |
| 9 | Glyphosate IPA | 1 |
|  | Mixture 2.2 | 1 |
|  | Water | 98 |
| 10 | Glyphosate IPA | 1 |
|  | Mixture 2.1 | 1 |
|  | Water | 98 |
| 11 (Comparison) | Glyphosate IPA | 1 |
|  | EMULSON ® GPE 3 SS | 1 |
|  | Water | 98 |

EXAMPLE 4
Measurement of the Superficial Tension

On the compositions 1–11 prepared as described in the above Example 3, the measurement of the superficial tension was carried out at a temperature of 20° C., according to the internal method UT 703, which corresponds to ASTM D1530 and D971.

The so-determined data of superficial tension in dyne/cm are reported in the following Table 2.

TABLE 2

| Composition | Superficial tension (dyne/cm) |
| --- | --- |
| 1 (Comparison) | 63.4 |
| 2 (Comparison) | 33.4 |
| 3 | 32.8 |
| 4 | 33.1 |
| 5 | 32.8 |
| 6 | 32.0 |
| 7 | 32.9 |
| 8 | 32.5 |
| 9 | 32.5 |
| 10 | 32.4 |
| 11 (Comparison) | 46.7 |

From the analysis of the data given in Table 2 it is clear that the surfactant mixtures of the invention decrease significantly the superficial tension of the compositions compared to those compositions which contain only surfactants known by the prior art.

The decrease of superficial tension results in a unexpectedly better effectiveness of said surfactant mixtures in dispersing homogeneously the pesticide active ingredients in the aqueous compositions, and/or in providing a uniform distribution of the sprayable compositions on the material to be treated.

EXAMPLE 5

Measurement of the Wetting Power

The wetting power of compositions 1, 2, 6, 10 and 11 prepared as described in Example 3, were determined by the following experimental tests.

The measurements were carried out at the temperature of 20° C. with determination of time of sinking of a cotton diskette according to the internal method NT/016, that refers to DIN 53901, and using the aforementioned compositions in diluted form with water in such a way that concentration of surfactant is 0.2% by weight.

The obtained data of the time of sinking, expressed in seconds, are given in the following Table 3.

TABLE 3

| Composition | Quantity of surfactant (% by wt.) | Time of sinking (seconds) |
| --- | --- | --- |
| 1 (Comparison) | — | >1800 |
| 2 (Comparison) | 0.2 | 392 |
| 6 | 0.2 | 44 |
| 10 | 0.2 | 40 |
| 11 (Comparison) | 0.2 | >1800 |

The experimental data reported in Table 3 show clearly that the time of sinking is notably reduced when the surfactants mixtures of the invention are used, as a lower sinking time corresponds to an increased wetting power of the compositions; therefore the data above reported give a measure of the velocity with which the pesticide compositions are distributed on the materials to be treated and of the penetration rate of the active ingredient into the treated surfaces.

What is claimed is:

1. Surfactant mixture to be used as wetting and/or emulsifying agents in pesticide agrochemical compositions comprising:

A) at least an alkylpolyglucoside,

B) at least an anionic derivative of an alkylpolyglucoside, and

C) at least an anionic derivative of a fatty alcohol.

2. The surfactant mixture according to claim 1, wherein the said alkylpolyglucoside is selected from alkylglucosides of formula (I)

$$R\text{—}O\text{—}(G)_x \quad (I)$$

where:

R is an aliphatic group, saturated or unsaturated, linear or branched, having from 6 to 20 atoms of carbon;

O is an oxygen atom;

G is a residue of a reducing saccharide connected to R—O by means of an ethereal O-glycosidical bond;

x is a number from 1 to 10, representing the average degree of oligomerization of G.

3. The surfactant mixture according to claim 2, wherein R is an alkyl group having from 8 to 16 atoms of carbon; G is a residue of glucose; and x is a number between 1 and 2.

4. The surfactant mixture according to claim 1, wherein the said anionic derivative of alkylpolyglucoside B) is selected from compounds of formula(II)

$$[R'\text{—}O\text{—}(G)_x]_n\text{—}(D)_y \quad (II)$$

where:

R' is an aliphatic group, saturated or unsaturated, linear or branched, having from 6 to 20 atoms of carbon;

O is an oxygen atom;

G is a residue of a reducing saccharide, connected to R'—O by means of an ethereal O-glycosidical bond;

D is an acyl residue connected to an oxygen atom of G, and derived from a bicarboxylic acid or polycarboxylic acid having an aliphatic chain with from 2 to 8 atoms of carbon, linear or branched, saturated or unsaturated, not substituted or substituted with one or more hydroxyl groups, and in which at least one carboxylic group is salified or in acid form;

x is a number between 1 and 10, representing the average degree of oligomerization of G;

n is a number between 1 and m—1, where m is the number of carboxylic groups in the acid that originates D;

y is a number between 1 to 10 representing the degree of average esterification of $(G)_x$.

5. The surfactant mixture according to claim 4, wherein R' is an alkyl group having from 8 to 16 atoms of carbon, G is a residue of glucose, and D is the acyl residue of a carboxylic acid selected among citric acid, tartaric acid, maleic acid and malic acid.

6. The surfactant mixture according to claim 5, wherein D is an acyl residue of citric acid with at least a salified carboxylic group.

7. The surfactant mixture according to the claim 1, wherein the said anionic derivative of a fatty alcohol C) is selected from the compounds of formula (III)

$$R''\text{—}O\text{—}D' \quad (III)$$

where

R'' is an aliphatic group, saturated or unsaturated, linear or branched, having from 6 to 20 atoms of carbon;

O is an oxygen atom;

D' is an acyl residue of a bicarboxylic acid or polycarboxylic acid, having an aliphatic chain with from 2 to 8 atoms of carbon, saturated or unsaturated, linear or branched, not substituted or substituted with one or more hydroxyl groups, and in which at least one carboxylic group is salified or in acid form.

8. The surfactant mixture according to claim 7, wherein R'' is an alkyl group having from 8 to 16 carbon atoms, and D' is an acyl residue of a carboxylic acid selected from the group consisting of citric acid, tartaric acid, malic acid and maleic acid.

9. The surfactant mixture according to claim 8, wherein D' is an acyl residue of citric acid with at least a salified carboxylic group.

10. The surfactant mixture according to claim 1, wherein: the said alkylpolyglucoside is selected from alkylpolyglucosides of formula (I)

$$R\text{—}O\text{—}(G)_x \quad (I);$$

the said anionic derivative of an alkylpolyglucoside is selected from compounds of formula (II)

$$[R'\text{—}O\text{—}(G)_x]_n\text{—}(D)_y \quad (II);$$

and the said anionic derivative of a fatty alcohol is selected from the compounds of formula (III)

$$R''\text{—}O\text{—}D' \quad (III)$$

wherein R, R' and R" are selected from aliphatic groups, saturated or unsaturated, linear or branched, having from 6 to 20 carbon atoms;

D and D' are selected from acyl residues of a bicarboxylic acid or polycarboxylic acid, having an aliphatic chain with from 2 to 8 carbon atoms, saturated or unsaturated, linear or branched, not substituted or substituted with one or more hydroxyl groups, and in which at least one carboxylic group is salified or in acid form;

O is an oxygen atom;

G is a residue of a reducing saccharide connected to R—O or R'—O by means of an ethereal O-glycosidical band;

x is a number from 1 to 10 representing the average degree of oligomerization of G;

n is a number between 1 and m−1, where m is the number of carboxylic groups in the acid that originates D;

y is a number between 1 to 10 representing the degree of average esterification of $(G)_x$.

11. The surfactant mixture according to claim 10, wherein R=R'=R".

12. The surfactant mixture according to claim 10, wherein D=D'.

13. The surfactant mixture according to claim 10, wherein R=R'=R" and, simultaneously, D=D'.

14. The surfactant mixture according to claim 1, wherein the amount of each component A), B) and C) ranges between 1 and 98% by weight with respect to the total weight of the mixture.

15. The surfactant mixture according to claim 14, wherein the amount of alkylpolyglycoside A) is comprised between 20 and 60% by weight with respect to the total weight of the mixture, the amount of the anionic derivative of alkylpolyglycoside B) is comprised between 20 and 50% by weight and the amount of the anionic derivative of fatty alcohol C) is comprised between 10 and 30% by weight.

16. Agrochemical composition with pesticide activity comprising the surfactant mixture according to claim 1, at least a pesticide active principle, and a carrier.

17. The composition according to claim 16, wherein the said active principle is in a form selected from the group consisting of wettable powders, dispersible granules, concentrated suspensions, concentrated emulsions, microemulsions, macroemulsions, microencapsulated products and solutions.

18. The composition according to claim 16, wherein the said active principle is selected from the group consisting of Acephate, Acetochlor, Alachlor, Alphacypermethrin, Amitraz, Atrazine, Benomyl, Bentazon, Bromacil, Captan, Carbaryl, Carbendazim, Carbofuran, Carboxin, Chloridazon, Chlorpyriphos, Chlorthalonil, Chlortoluron, Copper oxychloride, Copper oxyquinolate, Cypermethrin, Cyromazine, Dalapon, Deltamethrin, Diazinone, Dicamba, Dichlorprop, Dicofol, Dimethoate, Dinocap, Diuron, Dodine, Endosulfan, Ethofumesate, Ethylparathion, Fenitrothion, Fenthion, Fentin Hydroxide, Fluometuron, Folpet, Fosetyl-Al, Glufosinate, Glyphosate, Lindane, Linuron, Malathion, Mancozeb, MCPA, MCPB, Metalaxyl, Methamidophos, Methomyl, Methylparathion, Metobromuron, Metolachlor, Naled, Oxadiazon, Paraquat, Pendimethalin, Permethrin, Phenmedipham, Pyperonilbutoxide, Pirethrum, Propachlor, Propanil, Propiconazol, Propisochlor, Propoxur, Quizalofop-P-tefuryl, Sethoxydim, Simazine, Sulphur, Temephos, Tetraconazol, Tetramethrin, Thiophanate methyl, Thiram, Triadimefon, Triadimenol, Trifluralin, Vinclozolin, Zineb, Ziram, and the salts thereof.

19. The composition according to claim 18, wherein the said pesticide active principle is the isopropylammonium salt of Glyphosate.

20. The composition according to claim 16, further comprising one or more other active principles having an activity different from the pesticide, fertilisers, micronutrients, surfactants, antifoam agents, antifreeze agents, dyes, stabilisers, buffers, and other additives usually comprised in agrochemical compositions.

21. The composition according to claim 16, wherein the amount of the said surfactant mixture is comprised between 1 and 90% by weight with respect to the total weight of the composition, the amount of the said active principle is comprised between 1 and 90% by weight, and the amount of the said carrier is as much as to balance the composition.

22. The composition according to claim 16, wherein the amount of the said surfactant mixture is comprised between 0.1 and 20% by weight and the amount of the concentrated formulate comprising the pesticide active principle is comprised between 0.1 and 20% by weight with respect to the total weight of the composition.

23. Process for the preparation of an agrochemical composition comprising at least one pesticide active principle, wherein the improvement comprises adding to the said composition the surfactant mixture according to claim 1 as a wetting and/or emulsifying agent.

24. The process according to claim 23, wherein the said surfactant mixture is added to an aqueous composition of the said pesticide active principle, or it is added to a pesticide formulate which can be diluted with water to obtain the pesticide formulation to be spayed.

25. Method for the treatment of soil, seeds, plants and of any other biologic material which requires the application of pesticides, wherein the improvement comprises applying thereon the agrochemical composition according to claim 16.

* * * * *